US006596278B2

(12) United States Patent
Gander et al.

(10) Patent No.: US 6,596,278 B2
(45) Date of Patent: *Jul. 22, 2003

(54) IMMUNOLOGICAL RESPONSE POTENTIATION PROCESS

(75) Inventors: Bruno Gander, Immensee (CH); Giampietro Corradin, Lausanne (CH); Ying Men, Lausanne (CH); Claudio Thomasin, Rapperswil (CH); Hans Peter Merkle, Zurich (CH)

(73) Assignee: RMF Dictagene S.A., Lausanne (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 28 days.

(21) Appl. No.: 08/507,323
(22) PCT Filed: Dec. 23, 1994
(86) PCT No.: PCT/CH94/00242
§ 371 (c)(1),
(2), (4) Date: Oct. 11, 1995
(87) PCT Pub. No.: WO95/17167
PCT Pub. Date: Jun. 29, 1995

(65) Prior Publication Data
US 2002/0041879 A1 Apr. 11, 2002

(30) Foreign Application Priority Data
Dec. 23, 1993 (CH) .............................. 3849/93

(51) Int. Cl.[7] ...................... A61K 39/00; A61K 39/395; A61K 9/14
(52) U.S. Cl. ................. 424/193.1; 424/184.1; 424/192.1; 424/196.11; 424/197.11; 424/278.1; 424/280.1; 424/283.1; 424/489; 424/497; 424/499; 514/2; 530/300; 530/350
(58) Field of Search .................. 424/184.1, 192.1, 424/193.1, 196.11, 197.11, 278.1, 80.1, 283.1, 489, 497, 499; 514/2; 530/300, 350

(56) References Cited

U.S. PATENT DOCUMENTS

| 4,599,230 A | * | 7/1986 | Milich et al. ................ 424/89 |
| 4,803,070 A |   | 2/1989 | Cantrell et al. |
| 4,962,091 A | * | 10/1990 | Eppstein et al. ............... 514/2 |
| 5,008,116 A | * | 4/1991 | Cahn ......................... 424/491 |
| 5,417,986 A |   | 5/1995 | Reid et al. |
| 5,762,965 A | * | 6/1998 | Burnett et al. ............. 424/499 |
| 5,871,747 A | * | 2/1999 | Gengoux-Sedlik |
| 5,879,687 A | * | 3/1999 | Reed |
| 5,928,647 A | * | 7/1999 | Rock ..................... 424/196.11 |
| 6,004,763 A |   | 12/1999 | Gengoux et al. |
| 6,086,901 A |   | 7/2000 | O'Hagan et al. |
| 6,312,731 B1 |   | 11/2001 | Staas et al. |

FOREIGN PATENT DOCUMENTS

| GB | 2189143 | * | 10/1987 | |
| WO | WO91/07171 |   | 5/1991 | |
| WO | WO92/19263 | * | 11/1992 | .......... A61K/39/00 |
| WO | 98/33487 A1 |   | 8/1998 | |
| WO | 99/30737 A1 |   | 6/1999 | |
| WO | 00/12125 A1 |   | 3/2000 | |

OTHER PUBLICATIONS

Bertoletti et al., "HLA classI–restricted human cytotoxic T cells recognize endogenously synthesized hepatitis B virus nucleocapsid antigen", Proc. Natl. Acad. Sci, USA 88, 10445–10449 (1991).*
Warren et al., "Current Status of Immunological Adjuvants", Ann. Rev. Immunol. 4, 369–388 (1986).*
Eldridge et al. Mol. Immunol. 28(3): 287–294, 1991.*
Warren et al. Ann. Rev. Immunol. 4: 369–388, 1986.*
Amselem Ann. Rev. Immunol. 4: 369–388, 1986.*
Remington Pharmaceutical Sciences, 8th ed. pp. 271–272, 1990.*
Remingtons' Pharmaceutical Sciences 18th Ed. 1990 p 271–272.*
"Polymeric Biodegradable Liposheres (tm) as Vaccine Delivery Systems", Polymers for Advanced Technologies, vol. 3, No. 6, S. Amselem et al, Oct. 1992, Chichester (GB), pp. 351–357.
"O/W Emulsions as Carrries for Micronised Drug Particles", Manufacturing Chemist, vol. 63, No. 1, K.J. Steffens et al, Jan. 1992, Woolwich (GB), pp. 23–26.
"Parameters Affecting the Immunogenicity of Microencapsulated Tetanus Toxoid", Vaccine, vol. 10, No. 10, I. Esparza et al, Aug. 1992, London (GB), pp. 714–720.

* cited by examiner

Primary Examiner—Mary K. Zeman
(74) Attorney, Agent, or Firm—Burns, Doane, Swecker & Mathis, L.L.P.

(57) ABSTRACT

An immunological response potentiation process is disclosed for synthetic or genetically engineered antigens having low immunogenicity. The antigen is embedded into biodegradable microparticles, and the antigen-loaded microparticles are dispersed in a biodegradable medium. When parenterally administered, the antigen-loaded microparticles trigger a potentiated antibody, $T_H$-lymphocyte and $T_c$-lymphocyte response, as compared to an aqueous antigen solution. The extent of immunological potentiation is at least comparable with that attained by Incomplete Freund's adjuvant compositions. Linear B-$T_H$-cell epitopes, linear $T_c$-cell epitopes, dimers and multimers of those epitopes, and mixtures thereof, are used as low immunogenicity antigens. The microparticles are based on biodegradable biopolymers such as polyester, polyanhydride, and polyorthoester. By mixing microparticles with different wettabilities, swellabilities, release and biodegradation times, the most intense and longest immunological potentiation is achieved. This process is useful for immunizing humans and animals against diseases caused by viruses, bacteria, protozoa or tumor cells.

14 Claims, 5 Drawing Sheets

IMMUNOLOGICAL RESPONSE POTENTIATION PROCESS

This application is a national stage filing under 35 U.S.C. §371 of International Application No. PCT/CH94/00242 filed on Dec. 23, 1994, which International Application was not published by the International Bureau in English.

BACKGROUND OF THE INVENTION

1. Field of the Invention

The present invention relates to a process for potentiating the immunogenicity of synthetic, weakly immunogenic antigens. In what follows, synthetic, weakly immunogenic antigens are understood to be compounds having peptide or protein structures which are produced either chemically or by means of recombinant DNA technology and which, following parenteral administration in an aqueous solution or in the form of an aluminum adsorbate, only trigger an unimportant immunological response with very low antibody titers and lacking or only small T-cell proliferation. This group of antigens will hereinafter be called synthetic antigens for the sake of simplicity. By definition the immune response to the synthetic antigens herein described is therefore negligible if they are administered in an aqueous solution. Incomplete Freund's adjuvant (IFA) is used as an experimental reference preparation. IFA is a water in oil (W/O) preparation which is known to stimulate the humoral as well as the cellular immune response. However, IFA can only be used for testing purposes because of strong, undesirable side effects. By the term vaccine, formulations will hereinafter be understood which contain, in addition to the antigen, substances which themselves perform the function of purely inactive ingredients or an immunopotentiating function or even a combination of both functions. Purely inactive ingredients are, for example, water for dissolving the antigen for the parenteral administration, anti-microbial, isotonicity adjusting and pH-stabilizing inactive ingredients. Often immunipotentiating substances are called adjuvants, comprising, for example, insoluble aluminum salts (-phosphates, -hydroxides), certain lipopdlysaccharides, muramyl peptides, trehalose compounds, several cytokines, such as interleukine 1, lipophilic block copolymers (poloxamers). However, the experimental reference preparation incomplete Freund's adjuvant and several administration forms for vaccines, such as liposomes, emulsions, nano-capsules, also have adjuvant properties. These forms of administration not only cause the formation of an antigen deposit in vivo, but also have immune-stimulating properties.

2. Description of the Related Art

The development of new vaccines and the improvement of existing vaccine formulations has gained in importance and urgency in the past years (E. Eppstein et al., New Adjuvants for Vaccines Containing Purified Protein Antigens, Advances in Drug Delivery Review 4, 233–253, (1990)). The production of synthetic antigens as well as the development of suitable adjuvant formulations and forms of administration which increase the immunogenicity of weakly immunogenic compounds are in the forefront. The target of the development of new antigens is, on the one hand, diseases, such as AIDS, malaria, tuberculosis, cholera, hepatitis A, cancerous diseases, against which there are as yet no or only insufficiently active vaccines; on the other hand efforts are directed toward the replacement of the antigens contained in the traditional vaccines, such as inactivated viruses, bacteria or toxoids, by low-molecular peptides and proteins which are easier to produce and to purify and can be better characterized and which have the antigenic regions of the actual infectious agents in their structure. Such antigen peptides and proteins can be obtained at high purity biochemically or by means of recombinant DNA technology. This new generation of synthetic antigens has peptide sequences (epitopes) in its chemical structure which stimulate antigen-specific $T_H$- (helper), $T_C$- (cytotoxic) and B-lymphocytes. Hereby the so-called $T_H$-, $T_C$- and B-cell epitopes can each be individually present or can be covalently linked into a chimeral B-T epitope. Since these gene-technologically or chemically produced antigens have in general low molecular weights of approximately 500 to 2,000, their immunogenicity is very weak in contrast to toxoids of molecular weights of 50,000 to 150,000 or in contrast to particular antigens, such as inactivated viruses and other microorganisms.

Strategies for immunogenicity potentiation of synthetic antigens known up to now are based on increasing in a first step the molecular weight of these antigens by covalent linkage and, in a second step, on incorporating these higher molecular structures into immunopotentiating formulations.

It is known that an increase of the molecular weight can be achieved in that the synthetic antigen is covalently bound to high-molecular carrier proteins, such as diphtheria and tetanus toxoids, bovine serum albumin, keyhole limpet hemocyanin. These antigen carrier constructs, are disadvantageous because the employment of very expensive and relatively impure proteins from foreign organisms, because of the necessity for reactive and relatively toxic agents for the covalent linkage of the antigen and the carrier protein and because of the difficulty of purification as well as identity and purity testing of these compounds. On the other hand, it has also been proposed to increase the molecular weight of B-T epitopes by covalently linking them in a sort of branch structure to form multimers (J. P. Tam, Y.-A. Lu, Proceedings of the National Academy of Sciences of the USA 86, 9084–9088 (1989)). These constructs are called multiple antigen peptides, MAP in short.

It is further known that the combination of a B- and $T_H$-epitope is essential for an antibody formation to take place, and that the combination of a $T_C$-epitope with a $T_H$-epitope can improve the cytotoxic lymphocyte response, also called CTL response, after administration in IFA (C. Widman et al., J. Immunol. Methods 155, 95–99 (1992)).

Various immunopotentiating formulations for such weak immunogen antigens and their higher-molecular constructs are described in PS-EP-A1-513,861. O/W emulsions containing immune stimulants are a primary part thereof. Their inherent thermodynamic instability, which are reflected by the appearance of coalescence during storage, is disadvantageous in connection with these coarsely dispersed or colloid-dispersed systems. In addition, the components of such liquid-dispersed formulations suffer from chemical changes, such as oxidation and hydrolysis. The described formulations furthermore mostly require immune stimulants, such as muramyl peptides, which are not quite harmless toxicologically. Finally, these formulations do not show any long term effects at all. To obtain protection by vaccination over several years it is therefore necessary to inject these vaccine formulations three to four times in accordance with a defined vaccination schedule (so-called "booster" injections).

Furthermore, a system for the immune potentiation of antigens is known from the international publication WO 92/19263-A1, which employs so-called biodegradable microspheres, also called microcapsules or microparticles. It is disadvantageous with this method that the immune potentiation is mainly observed on the gastro-intestinal mucous membranes and therefore will probably show an effect only on relative few pathogens (so-called enterophatogenic microorganisms). The fact that the microparticles are administered in the duodenum and cannot be administered or taken perorally precludes a practical use, at least in humans. It furthermore appears in accordance with PS-EP-A2-333,523 that a balanced amount of fine (1 to 10 μm) and coarser (20 to 50 μm) microparticles seems to be an important prerequisite for the immune-potentiating effect. These requirements for the size range of the microparticles represent an additional effort during production and processing of the microparticles which appears to be disadvantageous.

OBJECTS OF THE INVENTION

It is the object of the invention to embed a synthetic antigen by means of specific biopolymers into biodegradable microparticles, to suspend these microparticles in a dispersion medium and to administer them parenterally, by means of which a potentiation of the systemic immunological response is caused.

In accordance with the invention this objective is attained by means of a process as set forth in the appended claims. Exemplary embodiments for this are described in Examples 1 to 6. The process of the invention will be explained in detail below by means of FIGS. 1 to 7.

DESCRIPTION OF THE PREFERRED EMBODIMENTS

1. Embedding Synthetic Antigen in Biodegradable Micro-Particles

The starting point of the process are synthetic antigens in accordance with the foregoing definition in the preamble, which contain in their known chemical structure at least one defined epitope of a pathogenic microorganism which can be recognized by the immune system. Hereby the epitope can be a B-cell epitope, a $T_H$-cell epitope, a $T_C$-epitope or an arbitrary mixture of these epitopes. The so-called multiple antigen peptides (MAP), alone or in combination with a $T_C$-epitope, preferably constitute the starting point of the process. The origin of the epitopes includes bacteria, viruses, protozoa and tumor cells. In accordance with the invention, the synthetic antigen is embedded into biodegradable microparticles. It is essential for the invention that biopolymers with specific physico-chemical properties are selected for producing the biodegradable microparticles. Important properties are wettability, insolubility, swelling and biodegradability of the biopolymers and the spherical microparticles produced therefrom in aqueous media and physiological liquids. The extent of swelling of the biodegradation and their biodegrading time greatly determine the release kinetics of the antigens from the microcapsules. It has now been surprisingly found that these release kinetics also affect the time course of the immune response. Examples of such biopolymers of varying wettability, swelling and biodegradation time are poly(lactic acid), poly(lactic-co-glycolic acid), poly(hydroxybutyric acid), poly(hydroxybutyric-co-valeric acid), poly(caprolacton). Embedding of the synthetic antigen into the biopolymer is performed by means of various known methods such as spray-drying, solvent evaporation or coacervation. Antigen-loaded, spherical microparticles of a size of 1 to 200 μm result from this.

2. Suspension in an Dispersion Medium

In the second step, the antigen-loaded microparticles in accordance with the invention are placed into a dispersion medium which is suitable for the parenteral administration of the microparticles. In this connection it is essential for the invention that the dispersion medium be biocompatible and biodegradable and in addition have advantageous properties for potentiating the immune response. Such advantageous dispersion media are, for example, aqueous or oily solutions of lecithin or aqueous-oily emulsions with lecithin at a concentration range of 0.1 to 20%, preferably 2 to 10%. Further suitable dispersion media are so-called microemulsions comprising a water, oil, tenside and co-tenside component. Biocompatible and biodegradable substances, such as natural or synthetic mono-, di- and triglycerides, lecithin, poloxamers and polasorbates are used for this. The dispersion media mentioned are characterized by surprisingly good wetting and suspension properties for the biodegradable microparticles. These wetting and suspension properties are for example considerably better than those of the usually employed dispersion media, such as carboxymethyl cellulose or solutions. The dispersion of the microparticles in the dispersion medium can be performed simply by shaking, by means of which an injectable preparation is created.

3. Administration

The antigen-loaded microparticles suspended in the suspension medium are administered parenterally, whereby this administration can take place once or several times at defined intervals. The latter form of administration is known under the term "booster". The first and second booster dose can be administered 1 to 4 weeks and 3 to 6 months after the initial injection, for example. A potentiated immune response lasting for several months is triggered following the single or multiple administration of the formulations in accordance with the invention.

4. Achieving the Potentiated Immune Response

The potentiation of the immune response is generally measured in BALB/c mice after a single, in exceptional cases also after a triple parenteral administration of the microparticles loaded with synthetic antigens in accordance with the invention. A MAP, produced from a universal $T_H$-epitope of the tetanus toxin (sequence 947 to 967) and a B-cell epitope of the repetitive region of the circumspgrozoite protein of Plasmodium berghei, as well a $T_C$-epitope of the circumsporozoite protein of Plasmodium berghei (sequence 252 to 260) are used as synthetic model antigens (S. Demotz et al., J. of Immunology 142, 394–402, (1989); P. Romero et al., Nature 341, 323 (1989); J. L. Weber et al.; Exp. Parasitology 63, 295 (1987)). The intensity and length of the immune potentiation is measured by means of the specific antibody titers, the T-lymphocyte proliferation and the specific cytotoxic T-lymphocyte activity. These three parameters are determined in accordance with known immunological methods.

Figure 1:
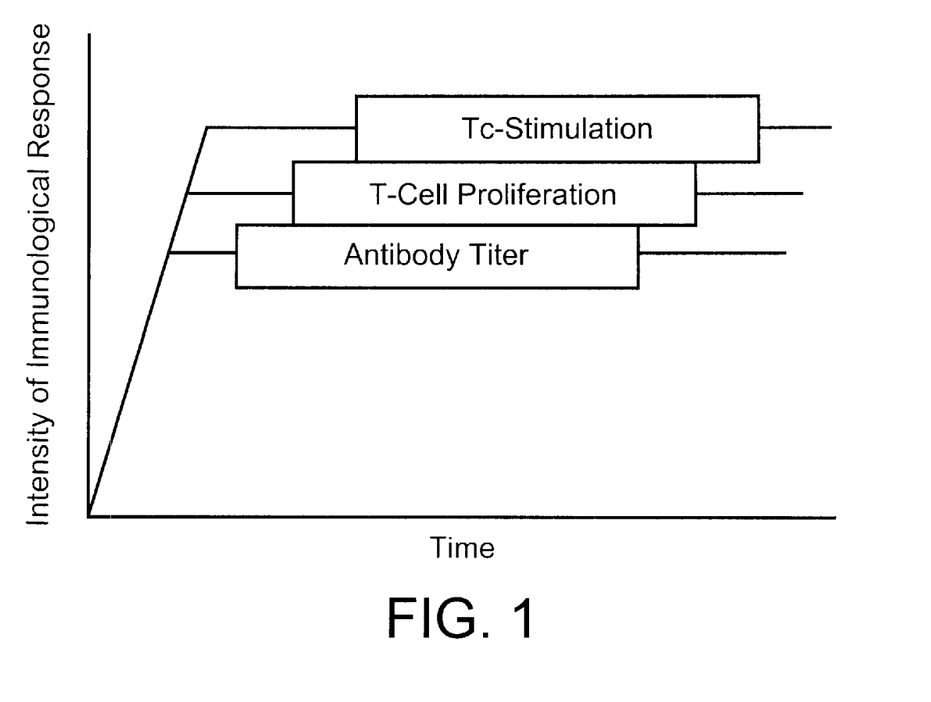
FIG. 1 illustrates a schematic representation of the immune potentiation in accordance with the invention.

FIG. 1 illustrates schematically the relevant parameters of the immune potentiation achieved by means of the process in accordance with the invention. According to the present invention, an immune potentiation means that the intensity during the time course of the immunological response as a result of an administered synthetic antigen has been potentiated with respect to an aqueous antigen solution and has been potentiated in a comparable or increased amount in respect to an IFA formulation on the levels of the antibody titer, the T-cell proliferation and the $T_C$-stimulation.

The possibility arises from this by means of mixing biopolymers of different wettability, swelling and biodegradation time to potentiate the humoral antibody response as well as the cellular T-lymphocyte response to an extent which is comparable or even greater than the potentiation achieved by means of incomplete Freund's adjuvant. In addition, the immune responses in accordance with this process can be time-controlled and are prolonged over several weeks in contrast to IFA and aqueous solutions.

Because of the custom-made properties of the biodegradable microparticles used, the process here described makes possible a specific potentiation of the humoral and cellular immune responses to synthetic antigens, in particular to so-called MAPS, which can be controlled in its progression over course time. Moreover, the process has the extraordinary advantage that it is possible to stimulate cytotoxic T-lymphocytes in addition to the specific and potentiated stimulation of B- and $T_H$-lymphocytes, because of which it is also possible to successfully provide immunization against viruses, protozoa and tumor cells in particular. It was surprisingly possible to demonstrate this cytotoxic stimulation of T-lymphocytes here for the first time. In contrast to the immune potentiation described in PS EP-A2-333,523 and PCT WO 92/19263, the present one is primarily systemic, i.e. not mucosal, and can be controlled in intensity as well as duration or progression over time. Furthermore, a narrow, exactly defined particle size distribution is not required for the immune potentiation, which entails technological advantages.

The process here described is used for the immunization of humans and animals against diseases caused by bacteria, viruses, protozoa and tumor cells. In particular the immunization against viruses, protozoa and tumor cells which can be achieved only in an unsatisfactory way with conventional vaccines, i.e. insufficiently and by accepting undesired side effects, represents a main application of this method. The stimulation of the cytotoxic T-cells by means of the process in accordance with the invention as well as the immune response lasting over an extended period of time constitute the basis for this application.

Example 1 describes the potentiation of the antibody response to the branched multiple antigen peptide identified as P30B2, which is constructed from a universal $T_H$-cell epitope of the tetanus toxin (sequence 947 to 967) and a B-cell epitope of Plasmodium berghei: 0.02 g P30B2 were dissolved in 2.00 g water and this solution was subsequently dispersed with the aid of an ultrasonic generator in a solution of 2.0 g poly(d, l-lactic acid co-glycolic acid) 50:50 (Resomer 502, Boehringer Ingelheim) in 40.0 g dichloromethane. Spherical microparticles (RG502) were produced from this dispersion by means of spray drying. Microparticles loaded with antigen were subsequently suspended in a 5% sterile solution of egg lecithin (Ovothin 170, Lukas Meyer, D-Hamburg) by shaking. This suspension was subcutaneously injected into a group of 8 BALB/c mice in respective amounts of 0.5 ml. The amount of antigen injected into each mouse was 30 µg. A second group of 8 BALB/c mice was immunized with the same amount of antigen in incomplete Freund's adjuvant (IFA) as a control. The antibody titers were determined by means of ELISA.

Figure 2:
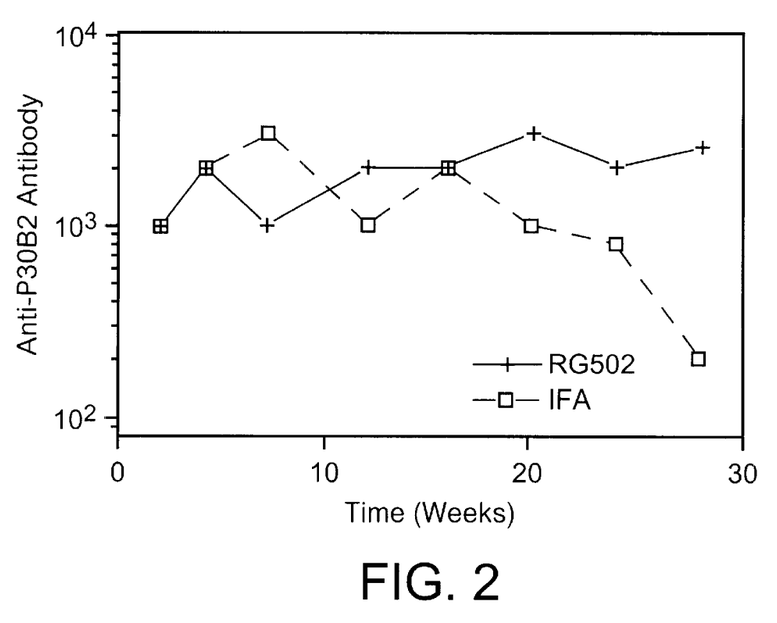
FIG. 2 illustrates antibody titers after a single administration of MAP in fast release microcapsules and in IFA formulation.

FIG. 2 shows the time course of the immune potentiation by RG502 in comparison to IFA, associated with Example 1. The antibody titers obtained from RG502 and IFA are comparable to each other during the first 15 weeks following immunization. After that the titers induced by IFA drop off, while the titers induced by the microcapsules remain constant over at least 28 weeks. Antibody titers of 1 to $2 \cdot 10^3$ were obtained already two weeks after administration of a hydrophilic, strongly swelling, fast-releasing and fast biodegradable biopolymer such as PLGA 50:50, and remain constant over a period of at least 28 weeks. In contrast thereto, the titers measured following a single administration of an IFA preparation drop off already after 15 weeks and after 28 weeks are only level at $2 \cdot 10^2$ after 28 weeks.

Example 2 describes the potentiation of the antibody response to the branched multiple antigen peptide of the designation P30B2 (in accordance with Example 1), constructed from a universal $T_H$-cell epitope of the tetanus toxin (sequence 947 to 967) and a B-cell epitope of the repetitive region of the circumsporozoite protein of Plasmodium berghei: 0.02 g P30B2 were dissolved in 2.00 g water and this solution was subsequently dispersed with the aid of an ultrasonic generator in a solution of 2.0 g poly (d, l-lactic acid) (Resomer 206, Boehringer Ingelheim) in 40.0 g dichloromethane. Spherical microparticles (R206) were produced from this dispersion by means of coacervation, induced by the addition of silicon oil. Microparticles loaded with antigen were subsequently suspended in a 5% sterile solution of egg lecithin (Ovothin 170, Lukas Meyer, D-Hamburg) by shaking. This suspension was subcutaneously injected into a group of 8 BALB/c mice in respective amounts of 0.5 ml. The amount of antigen injected into each mouse was 30 µg. A second group of 8 BALB/c mice was immunized with the same amount of antigen in incomplete Freund's adjuvant (IFA) as a reference. The antibody titers were determined by means of ELISA.

Figure 3:
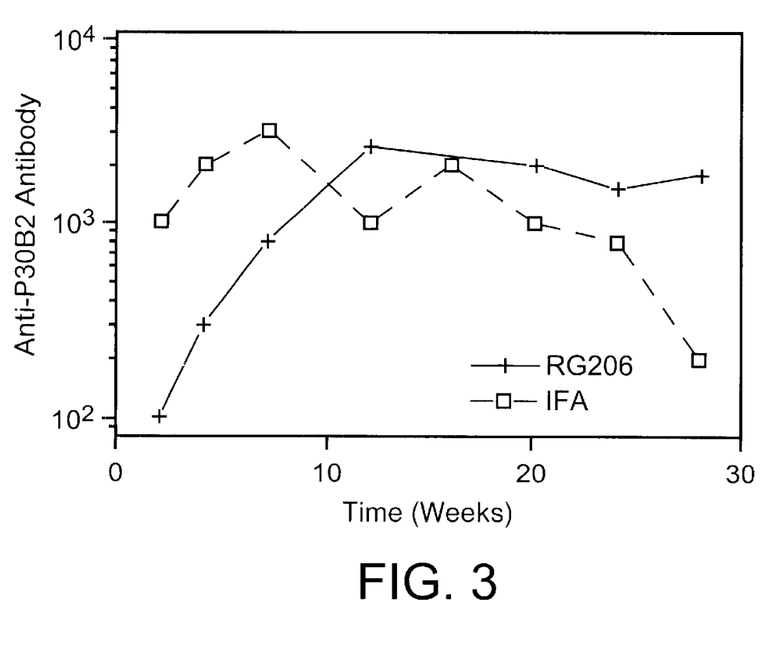
FIG. 3 illustrates antibody titers after a single administration of MAP in slow-release microcapsules and an IFA formulation.

FIG. 3 shows the time course of the immune potentiation by R206 in comparison to IFA, associated with Example 2. The antibody titers obtained from the hydrophobic, weakly swelling, slow-release and slowly biodegradable R206 continuously rise during the first 12 weeks and then reach the level which had been achieved with IFA already 2 weeks after immunization. While the IFA titers drop again steadily after approximately 15 weeks, the R206 titers remain constant over a period of at least 28 weeks.

Example 3 describes the potentiation of the antibody response to the branched multiple antigen peptide of the designation P30B2 (in accordance with Example 1), constructed from a universal $T_H$-cell epitope of the tetanus toxin (sequence 947 to 967) and a B-cell epitope of the repetitive region of the circumsporozoite protein of Plasmodium berghei: analogously to Example 1, P30B2 was incorporated into poly (d, l-lactic acid-co glycolic acid) 75:25 (Resomer RG752, Boehringer Ingelheim) and processed into spherical microparticles (RG752). Microparticles of RG752, RG502

(from example 1) and R206 (from Example 2) containing identical amounts of P30B2 were suspended in a 5% sterile solution of egg lecithin (Ovothin 170, Lukas Meyer, D-Hamburg) by shaking. This suspension was subcutaneously injected into a group of 8 BALB/c mice in respective amounts of 0.5 ml. The amount of antigen injected into each mouse was 30 µg. A second group of 8 BALB/c mice was immunized with the same amount of antigen in incomplete Freund's adjuvant (IFA) as a control. The antibody titers were determined by means of ELISA.

Figure 4:
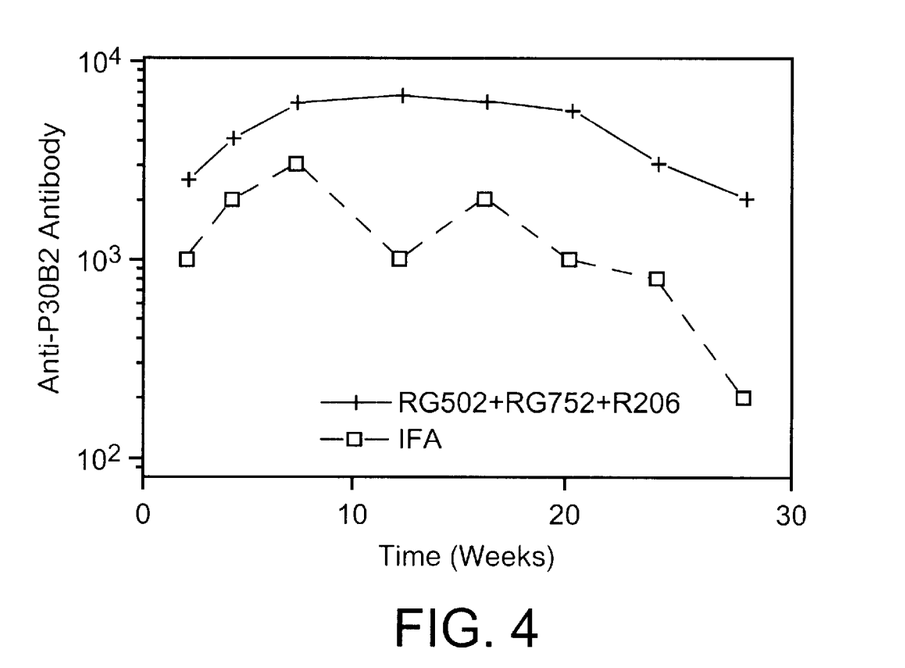
FIG. 4 illustrates antibody titers after a single administration of MAP in a mixture of fast- and slow-release microcapsules and an IFA formulation.

FIG. 4 shows the time course of the immune potentiation obtained with a mixture of RG506, RG752 and R206 in comparison to IFA, associated with Example 3. The antibody titers obtained from this microcapsule mixture of fast- and slow-release biopolymers rises quickly and reaches after two weeks a level higher by a factor of 2.5 than the antibody titers achieved with IFA. While the IFA titers drop again steadily after approximately 15 weeks, the titers achieved with the microcapsule mixture remain relatively constant over a period of at least 28 weeks.

Example 4 describes the potentiation of the antibody response to the branched multiple antigen peptide of the designation P30B2 (in accordance with Example 1), constructed from a universal $T_H$-cell epitope of the tetanus toxin (sequence 947 to 967) and a B-cell epitope of the repetitive region of the circumsporozoite protein of Plasmodium berghei: analogously to Example 1, P30B2 was incorporated into poly (d, l-lactic acid-co glycolic acid) 50:50 (Resomer RG502, Boehringer Ingelheim) and processed into spherical microparticles (RG502). The microparticles loaded with antigen were suspended in a 5% sterile solution of egg lecithin (Ovothin 170, Lukas Meyer, D-Hamburg) by shaking. This suspension was subcutaneously injected into a group of 8 BALB/c mice in respective amounts of 0.5 ml. The amount of antigen injected into each mouse was 3×10 µg. The injection was repeated after 16 days (first booster) and 113 days (second booster). A second group of 8 BALB/c mice was immunized with the same amount of antigen in incomplete Freund's adjuvant (IFA), used as reference and according to the same vaccination schedule. The antibody titers were determined by means of ELISA.

Figure 5:
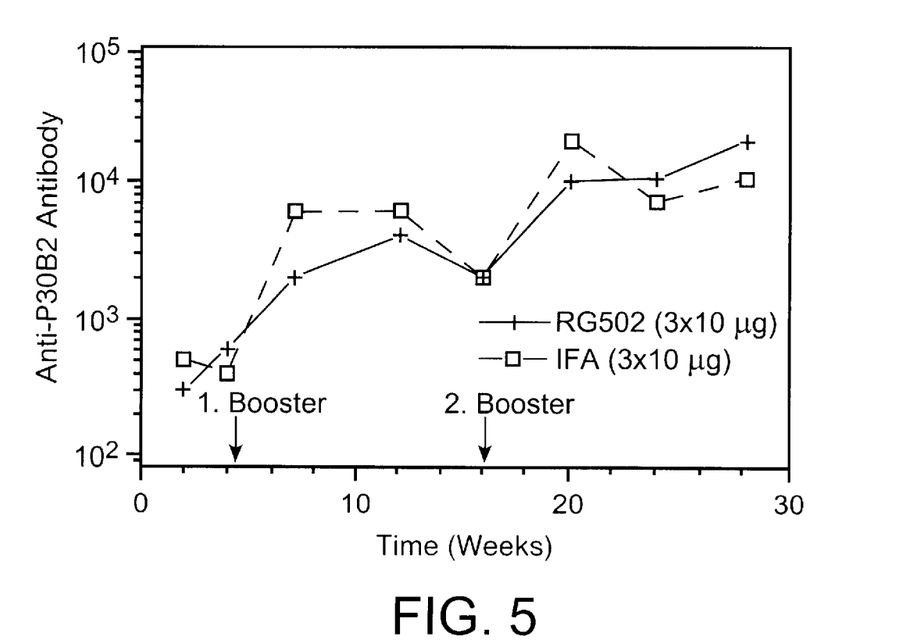
FIG. 5 illustrates antibody titers after a triple administration of MAP in fast-release microcapsules and an IFA formulation.

FIG. 5 shows the time course of the immune potentiation after booster injections with RG502 in comparison to IFA, associated with Example 4. The antibody titers obtained from RG502 and IFA rise comparatively. Accordingly, the process in accordance with the invention is also suitable for the immune potentiation achieved by boosters.

Example 5 describes the potentiation of the $T_H$-lymphocyte proliferation to the multiple antigen peptide of the designation P30B2 in accordance with Examples 1 to 4. P30B2 was incorporated into RG502, RG752 and R206 analogously to the Examples 1, 2 and 3 and processed into spherical microparticles of different degrees of swelling. Identical amounts of microparticles containing P30B2 were suspended in a 5% sterile solution of egg lecithin (Ovothin 170, Lukas Meyer, D-Hamburg) by shaking. This suspension was subcutaneously injected into a group of 8 BALB/c mice in respective amounts of 0.5 ml. The amount of antigen injected into each mouse was 30 µg. A second group of 8 BALB/c mice was immunized with the same amount of antigen in incomplete Freund's adjuvant (IFA) as a reference. The T-cell proliferation in the lymph nodes was determined in a known manner.

Figure 6:
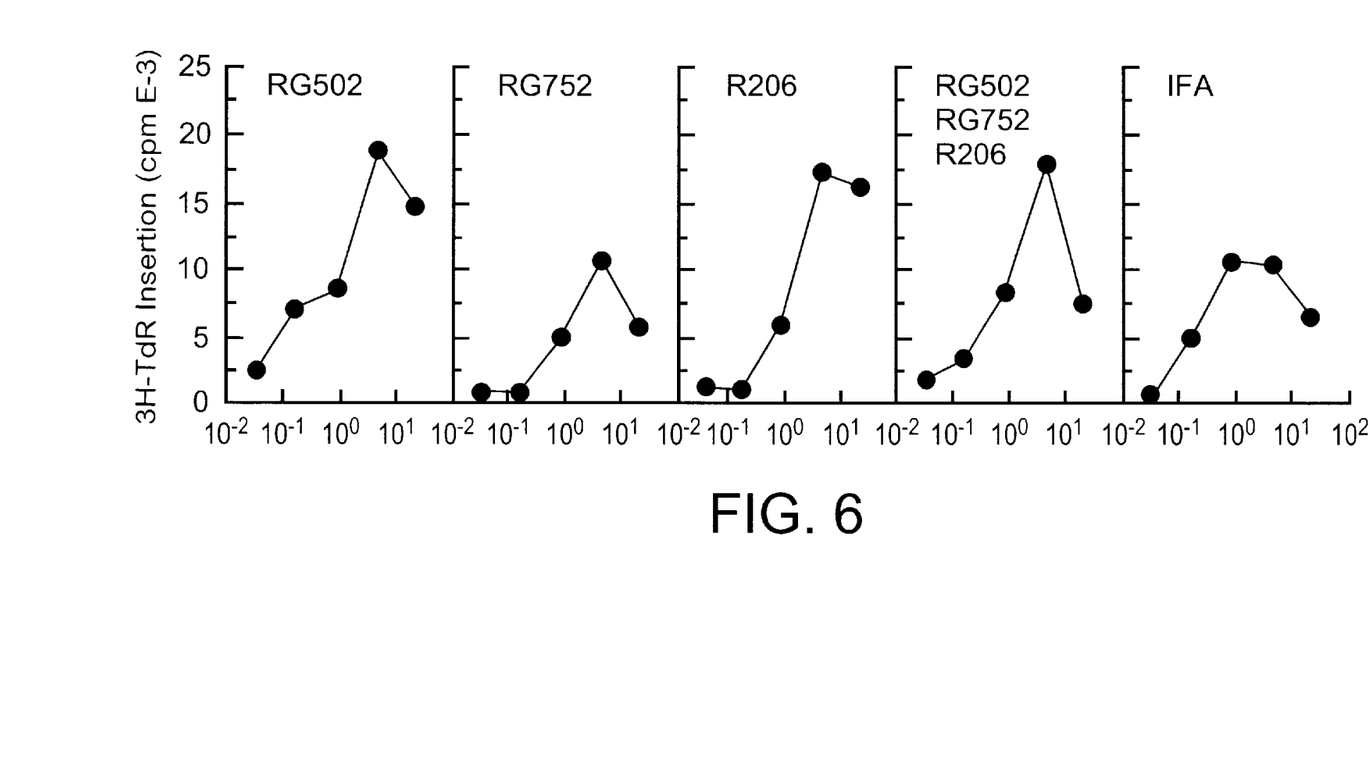
FIG. 6 illustrates Proliferative T-lymphocyte response after a single administration of different, MAP-containing microcapsules and an IFA formulation.

FIG. 6 shows the T-lymphocyte proliferation described in Example 5 14 days after the administration of various microcapsule formulations as well as of an IFA preparation. It can be seen from this that all microcapsule formulations, i.e. RG502 with fast antigen release, RG752 with an antigen release of medium rate and R206 with a low antigen release rate, as well as the mixture of all three microcapsule types, all potentiate the T-lymphocyte proliferation in an at least comparable, sometimes even greater extent than an IFA preparation.

Example 6 describes the triggering of a cytotoxic T-lymphocyte reaction to a $T_C$ cell epitope of the circumsporozoite protein of Plasmodium berghei (CTL 359A, sequence 252 to 260): 0.008 g of CTL 359A were dissolved in 1.0 g of water and this solution was subsequently dispersed by means of an ultrasonic generator in a solution of 4.0 g poly (d, l-lactic acid-coglycolic acid) (Resomer 502, Boehringer Ingelheim) in 60.0 g dichloromethane. Spherical microparticles were produced by means of spray drying. The microparticles loaded with CTL 359A were mixed with microparticles loaded with P30B2 in accordance with Example 1 in a ratio of CTL 359A:P30B2 of 1:10 to increase the immune response to CTL 359A. The mixture of the microcapsules was subsequently suspended in a 5% sterile solution of egg lecithin (Ovothin 170, Lukas Meyer, D-Hamburg) by shaking. This suspension was subcutaneously injected into a group of 2 BALB/c mice in respective amounts of 0.5 ml. The amount of antigen injected into each mouse was 4 µg of CTL 359A and 40 µg of P30B2. The $T_C$-cell response was determined after 10 and 20 days by means of a cell lysis test.

Figure 7:
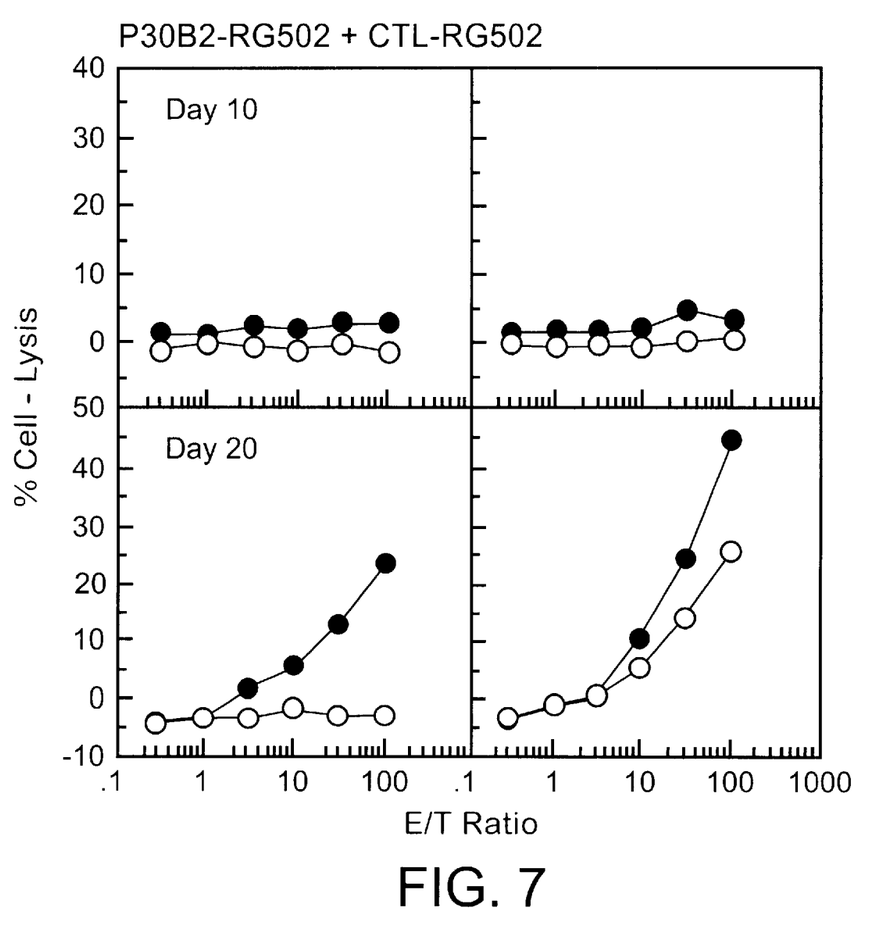
FIG. 7 illustrates $T_C$-response after a single administration of a mixture of fast-release microcapsules containing respectively a synthetic $T_C$-antigen and a related MAP.

FIG. 7 shows the $T_C$-lymphocyte response associated with Example 6, which was determined 10 and 20 days after immunization, or administration of the formulations. The percentile cell lysis activity is represented as a function of the effect/target cell ratio E/T. In a surprising manner, the simultaneous administration of microencapsulated $T_C$ epitope and $T_H$ epitope (P30B2+CTL359A in RG502) induces a significant $T_C$-lymphocyte stimulation which can be observed 20 days after administration. The time course of the $T_C$ response which, in contrast to the $T_H$ and antibody responses requires a considerably longer time, appears to be of particular interest.

It is essential for the invention that biodegradable spherical microparticles are proposed which potentiate the immune response to synthetic antigens. By determining the physico-chemical properties of the biopolymers used it is possible to control the extent and time course of this immune potentiation. The process furthermore makes it possible to stimulate also the cytotoxic T-lymphocytes in addition to the antibody and $T_H$-lymphocyte potentiation. The extent of immune potentiation is at least comparable to the potentiation achieved by means of IFA preparations and its time course is clearly prolonged. A process is therefore available which can be employed in the immunization of humans and animals against diseases caused by viruses, bacteria, protozoa or tumor cells.

What is claimed is:

1. A method for potentiation of the immunological response of humans and animals to at least one cytotoxic T-lymphocyte (CTL) antigen, comprising:
    dispersing the cytotoxic T-lymphocyte (CTL) antigen in a solution comprising at least one biocompatible biopolymer to form a dispersion;
    forming a spherical microparticle comprising the antigen embedded therein;
    suspending the spherical microparticles comprising the antigen in a carrier medium; and
    parenterally administering the preparation thus obtained to a human or animal in need thereof in order to initiate, potentiate and prolong a cytotoxic T-lymphocyte response, wherein said antigen induces a negligible and nonprotective immune response if administered as aqueous solution.

2. A method for potentiation of the immunological response of humans and animals to at least one cytotoxic T-lymphocyte (CTL) antigen comprising:

dispersing the cytotoxic T-lymphocyte (CTL) antigen in a solution comprising at least one biocompatible biopolymer to form a dispersion;

forming a spherical microparticle comprising the antigen embedded therein;

suspending the spherical microparticles comprising the antigen in a carrier medium; and parenterally administering the preparation thus obtained to a human or animal in need thereof in order to initiate, potentiate and prolong a cytotoxic T-lymphocyte response, wherein said antigen induces a negligible and non-protective immune response if administered as aqueous solution and said biopolymer is selected from the group consisting of poly(lactic acid), poly(glycolic acid), poly (lactic-co-glycolic acid), polycaprolactone, poly (hydroxybutyric acid), poly(hydroxybutyric-co-valeric acid), poly(orthoester) and poly(anhydrides).

3. A method according to claim 1, wherein said antigen comprises at least one cytotoxic T-lymphocyte ($T_c$) epitope.

4. A method according to claim 1, wherein said antigen comprises at least one cytotoxic T-lymphocyte ($T_c$) epitope physically mixed or chemically linked with at least one helper T-lymphocyte ($T_h$) epitope.

5. A method according to claim 1, wherein said antigen comprises at least one cytotoxic T-lymphocyte ($T_c$) epitope, at least one helper T-lymphocyte ($T_h$) epitope, and at least one B-lymphocyte epitope, wherein said epitopes are physically mixed or chemically linked.

6. A method according to claim 1, wherein said antigen is derived from protozoa, viruses, bacteria, tumor cells, or combinations thereof.

7. A method according to claim 1, wherein said spherical microparticles are constructed from a biopolymer derived from a member of the group consisting of poly(lactic acid), poly(glycolic acid), poly(lactic-co-glycolic acid), polycaprolactone, poly(hydroxybutyric acid), poly (hydroxybutyric-co-valeric acid), poly(orthoester) and poly (anhydrides).

8. A method according to claim 1, wherein said biopolymer is derived from at least two members of the group consisting of poly(lactic acid), poly(glycolic acid), poly (lactic-co-glycolic acid), polycaprolactone, poly (hydroxybutyric acid), poly(hydroxybutyric-co-valeric acid), poly(orthoester) and poly(anhydrides).

9. A method according to claim 1, wherein an aqueous or oily lecithin solution is used as the dispersion medium.

10. A method according to claim 1, wherein said antigen is obtained by a chemical process or by a recombinant process.

11. A method according to claim 1, wherein said antigen comprises at least one cytotoxic T-lymphocyte ($T_c$) peptide epitope having a molecular weight ranging from about 500 to about 2000.

12. A method according to claim 1, wherein said antigen is derived from protozoa.

13. The method according to claim 1, wherein said spherical microparticle having the antigen embedded therein is formed by a method selected from the group consisting of spray-drying, solvent evaporation and coacervation.

14. The method of claim 2, wherein said spherical microparticle comprising the antigen embedded therein is formed by a method selected from the group consisting of spray-drying, solvent evaporation and coacervation.

* * * * *